United States Patent [19]

Dahmén et al.

[11] Patent Number: 4,521,592
[45] Date of Patent: Jun. 4, 1985

[54] COMPOUNDS FOR THERAPEUTIC OR DIAGNOSTIC USE, A PROCESS AND INTERMEDIATES FOR THEIR PREPARATION

[75] Inventors: Jan E. Dahmén, Åkarp; Hans G. Magnusson, Staffanstorp; Kaj B. Mårtensson, Lund, all of Sweden

[73] Assignee: Svenska Sockerfabriks AB, Malmö, Sweden

[21] Appl. No.: 419,314

[22] Filed: Sep. 17, 1982

[30] Foreign Application Priority Data

Oct. 23, 1981 [SE] Sweden .............................. 8106279-6
Apr. 2, 1982 [SE] Sweden .............................. 8202144-5

[51] Int. Cl.$^3$ ............................................. C07H 15/04
[52] U.S. Cl. ........................................ 536/4.1; 536/1.1
[58] Field of Search ............................ 536/1.1, 4.1, 119

[56] References Cited

U.S. PATENT DOCUMENTS

| | | | |
|---|---|---|---|
| 4,147,860 | 4/1979 | Farnham et al. | 536/119 |
| 4,156,777 | 5/1979 | Kimura | 536/4.1 |
| 4,359,458 | 11/1982 | Nair et al. | 536/1.1 |

FOREIGN PATENT DOCUMENTS

| | | | |
|---|---|---|---|
| 0109960 | 8/1979 | Japan | 536/4.1 |
| 2075502 | 11/1981 | United Kingdom | 536/119 |

OTHER PUBLICATIONS

Fieser et al., *Organic Chemistry*, 2nd ed., Boston: D. C. Heath and Company, 1950, pp. 179 & 177.
Pigman, *The Carbohydrates*, N.Y.: Academic Press Inc., 1957, pp. 107, 140, 208.
Fieser et al., *Reagents for Organic Synthesis*, vol. 1, (1967), pp. 530–532 and 1049–1050.
Santaniello et al., *J. Org. Chem.*, (1983), pp. 3074–3075.

*Primary Examiner*—Johnnie R. Brown
*Assistant Examiner*—Elli Peselev
*Attorney, Agent, or Firm*—Burns, Doane, Swecker & Mathis

[57] ABSTRACT

Novel compounds having the general formula (I):

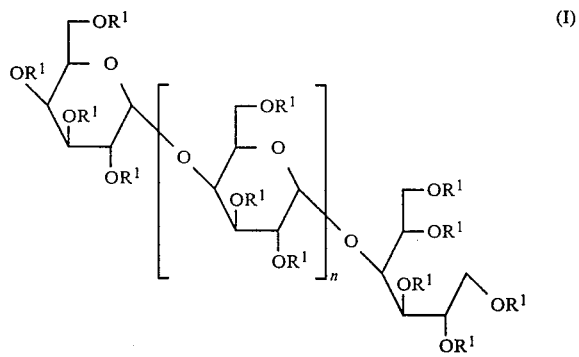

wherein $R^1$ is hydrogen or an acyl group; and n is an integer of up to 10 including zero; novel compounds having the general formula (II):

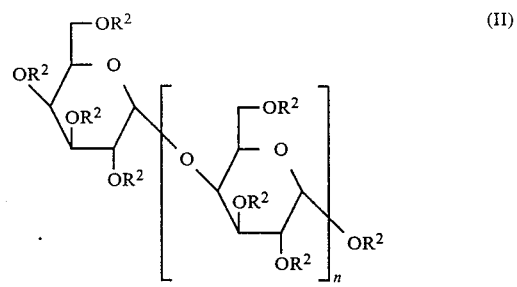

wherein $R^2$ is hydrogen or an acyl group, and wherein the group $OR^2$ at C-atom 1 of the reducing end of the molecule is in either α- or β-configuration; and n is an integer from 2 to 10, inclusive; a process for preparing compounds (II).

9 Claims, No Drawings

COMPOUNDS FOR THERAPEUTIC OR DIAGNOSTIC USE, A PROCESS AND INTERMEDIATES FOR THEIR PREPARATION

TECHNICAL FIELD

The present invention relates to new and novel compounds for therapeutic or diagnostic use and to processes and intermediates for their preparation. More particularly, the invention resides in new carbohydrates of an oligo-saccharidal nature, and their preparation.

TECHNICAL BACKGROUND

During the last few years, the phenomenon of bacterial attachment to host epithelial cells has become of great interest (Ref. 1). Two Swedish groups (Ref. 2 and 3) have suggested that the di-galactose compound of formula 1 below should act as a receptor in the attachment of fimbriated uropathogenic *Coli* bacteria to the surface of urinary-tract epithelial cells in humans. Moreover, the di-galactose moiety is considered to be present on the surface of the epithelial cells in the form of trihexosylceramide (formula 2 below) and globoside.

Furthermore, the digalactose-containing glycolipid "galabiosyl ceramide" (formula 3 below) is present in kidney tissue (Ref. 4), although the function of the compound is not known.

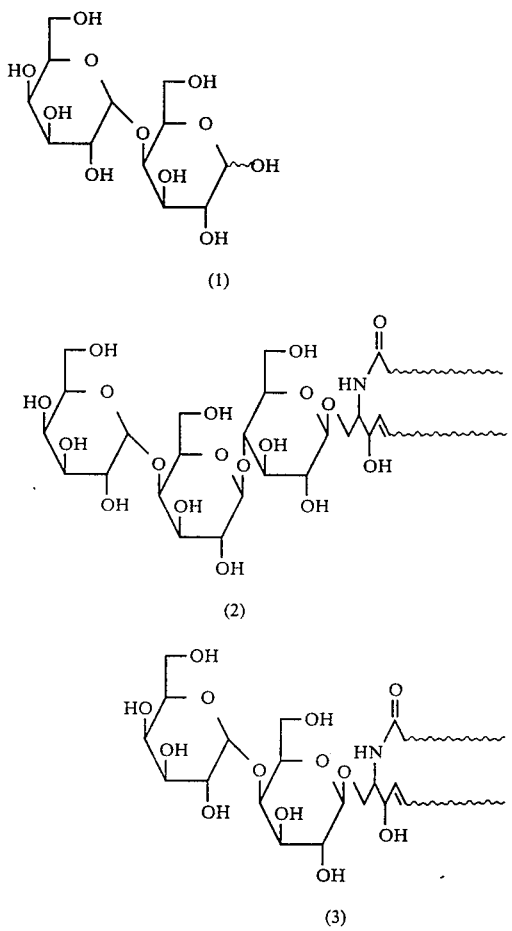

Simple glycosides (e.g. methyl and p-nitrophenyl) of compound 1 and of the trisaccharide moiety of compound 2 have been shown to inhibit the agglutination of uropathogenic *Coli* bacteria with certain rod blood cells (Ref. 1). This indicates the use of compound 1 for the preparation of novel types of diagnostic reagents and also of therapeutics having a novel kind of activity compared with traditional antibiotics i.e. inhibition of bacterial attachment to epithelium instead of killing the bacteria.

BACKGROUND ART

In literature, methods have been reported for the preparation of 4-O-α-D-galactopyranosyl-D-galactose (1) and derivatives thereof.

Compound 1 has been prepared from di-galacturonic acid (4) according to Scheme 1 below (Ref. 5).

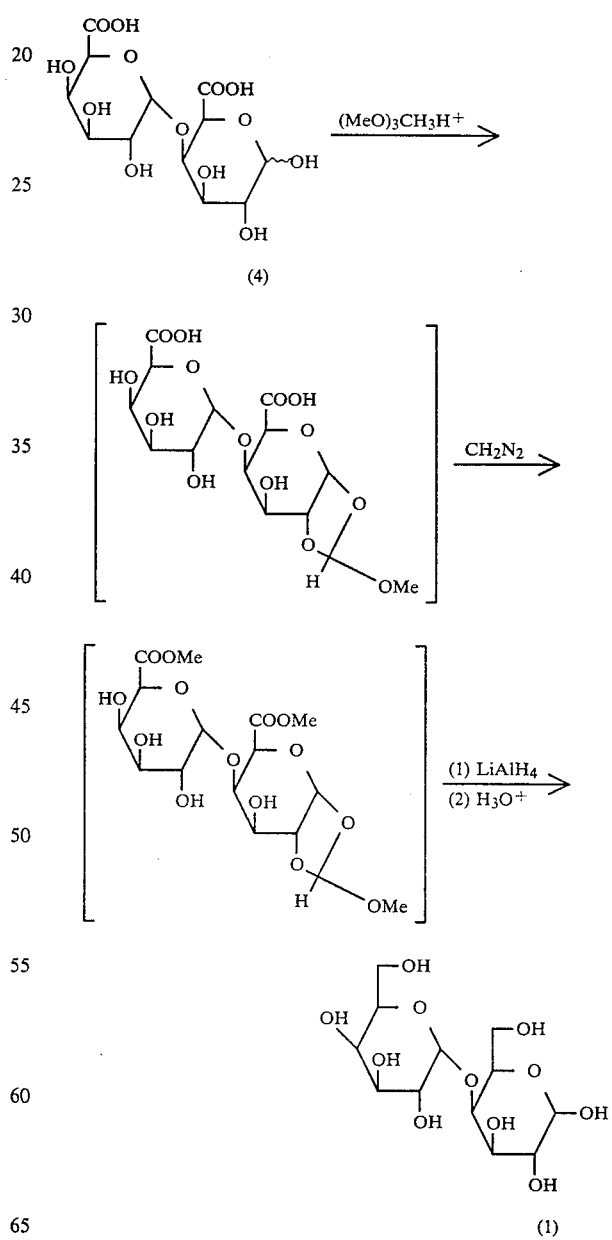

However, the obnoxious reagents used (e.g. diazomethane, lithium aluminum hydride) prohibit any large-scale preparation of compound 1 according to this route. A variation of this reaction sequence has also been reported (Ref.6).

The fully acetylated derivative of compound 1 has been prepared (Ref. 7, 8, 9) by multi-step reaction sequences, starting with galactose, as exemplified in Scheme 2 below (Ref. 7). Also in these cases, some of the reagents used (e.g. mercuric cyanide) together with the low over-all yield will make large scale preparation impractical.

Scheme 2

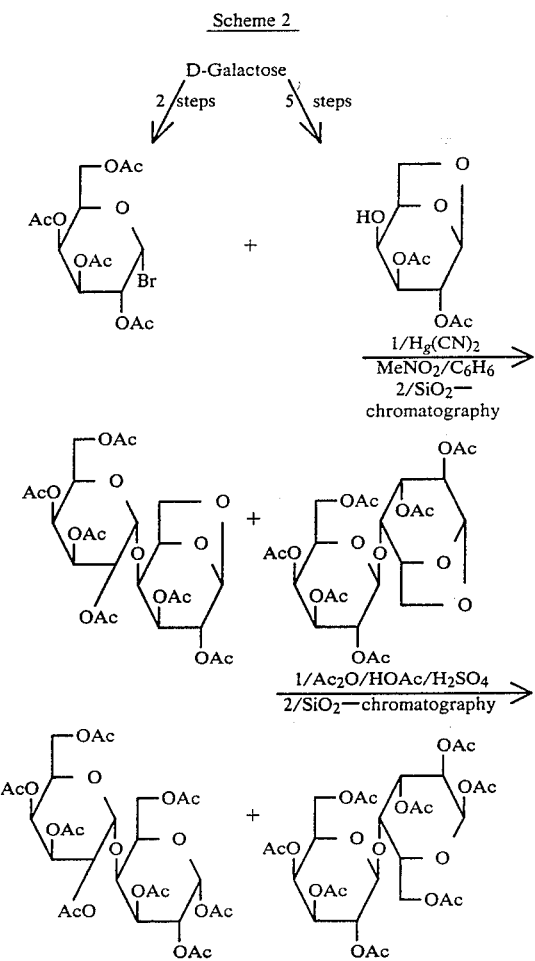

SUMMARY OF THE INVENTION

It is seen from the state of art as referred to above that there is a need for new processes for synthesizing oligosaccharides of different types and from readily available starting materials. Thus, the invention has for its principal object to provide new and novel compounds useful for medicinal and diagnostic purposes as indicated above.

Another object of the invention is to provide new and novel intermediates useful for making such new compounds.

Yet another object is to provide a process for preparing the new and novel compounds of therapeutic or diagnostic use.

According to one aspect of the invention there are provided new and novel compounds having the general formula (II):

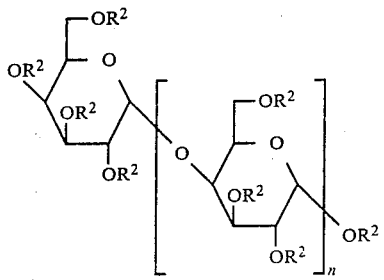

wherein $R^2$ is hydrogen or an acyl group; and n is an integer from 2 to 10, inclusive.

$R^2$ is preferably selected from the group consisting of formyl, acetyl, propionyl, trifluoro acetyl, and benzoyl. Under the definition of $R^2$, acetyl is particularly preferred and n is suitably equal to 2.

According to another aspect of the invention there are provided new and novel compounds useful as intermediates for preparation of compounds of the formula (II) and having the general formula (I):

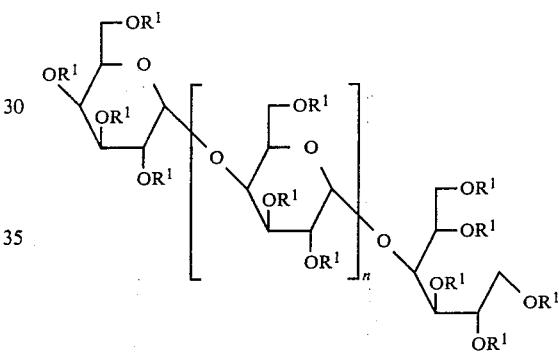

wherein $R^1$ is hydrogen or an acyl group; and n is an integer of up to 10 including zero.

$R^1$ is preferably selected from the group consisting of formyl, acetyl, propionyl, trifluoro acetyl, and benzoyl. The preferred meaning of $R^1$ is acetyl and n is suitably 1 or 2, particularly 1.

According to a third aspect of the invention there is provided a process for preparing compounds of formula (II) above, wherein n is 1–10, said process comprising reducing a compound of formula (III):

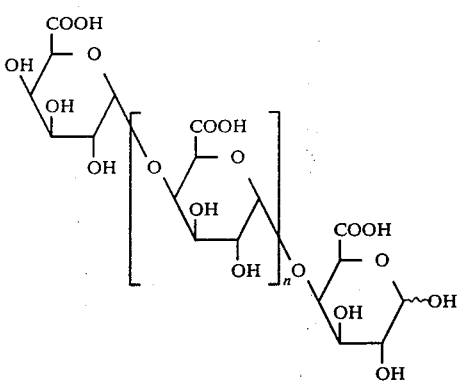

wherein the carboxyl groups are fully esterified and n has the above meaning, to form a compound of formula (IV):

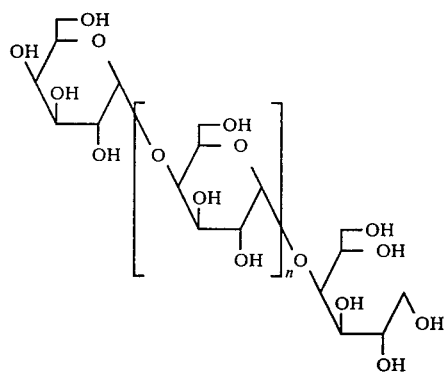

(IV)

wherein n has the above meaning. Compound IV is then subjected to hydrolysis to form compound II, wherein $R^2$ is hydrogen. Alternatively, the compound of formula (IV) may be subjected to acylysis to form the compound of formula (II), wherein $R^2$ is an acyl group, the resulting compound being then, if desired, hydrolysed to form the compound of formula (II), wherein $R^2$ is hydrogen.

According to a fourth aspect of the invention there is provided a process for preparing compounds of formula (II) above, wherein n is an integer of up to 10 including zero, said process comprising reducing a compound of formula (V):

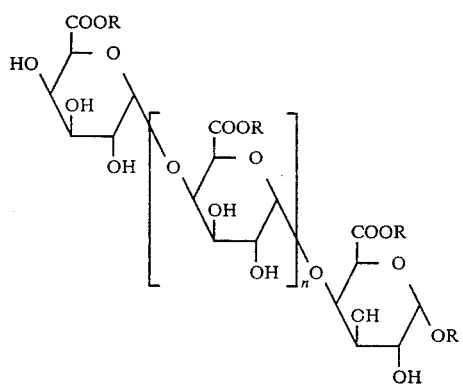

V wherein n is an integer of up to 10 including zero, R is an alkyl group, preferably lower alkyl, and the aglycone (OR) and the alcohol part of the ester functions (OR) are all derived from the same alcohol, to form new and novel compounds of formula (VI):

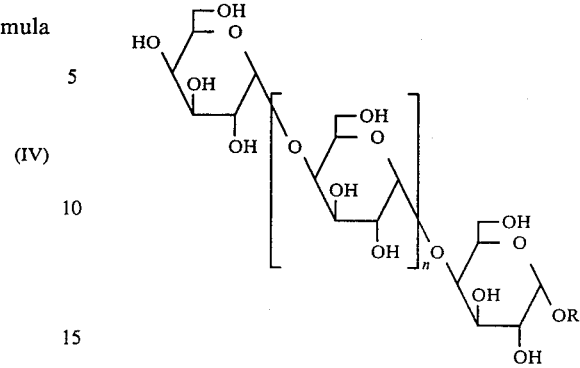

VI wherein n and R have the above meaning.

R is preferably selected from the group consisting of methyl, ethyl, propyl and butyl. The preferred meaning of R is methyl and n is suitably zero or one, particularly zero. Compound VI is then subjected to hydrolysis to form compound II, wherein $R^2$ is hydrogen and n is an integer of from 1 to 10, inclusive. Alternatively, the compound of formula (VI) may be subjected to acylysis to form the compound of formula (II), wherein $R^2$ is an acyl group and n is an integer of up to 10 including zero, the resulting compound being then, if desired, hydrolysed to form the compound of formula (II), wherein $R^2$ is hydrogen and n is an integer of up to 10 including zero.

The first part of said process is preferably carried out in a hydroxylic solvent, and the reduction of the fully esterified compound III is suitably provided by the use of sodium borohydride or sodium cyano borohydride as a reducing agent.

The acylysis of compound IV is preferably carried out by using acetic anhydride together with a strong acid. Among such strong acids there may be mentioned sulphuric acid.

The term "acylysis" as used herein refers to scission of one (or several) glycosidic bond(s), replacing cleaved-off moieties by acyl and/or acyloxy groups. Esterification of hydroxyl groups by acylation, i.e. replacing the hydrogen atoms by acyl groups, may occur simultaneously under the conditions used for acylysis.

One of the advantages of the process of the invention as outlined above is the fact that pectin can be used as an original starting material. As is well known, pectine is one of the few naturally occurring compounds containing the desired α-1,4 linkage and, furthermore, it is an inexpensive and readily available starting material. Pectine is suitable for larger-scale preparation of the new and novel compounds of this invention, and below in schemes 4 and 5 there is given a summary of the overall-process for preparing α- and β-glycosides for interesting medicinal and other applications. In scheme 4 the hydrolysis product of pectine (step a) is exemplified by tri-galacturonic acid, but it is to be understood that hydrolysis of pectine may well result in other oligomers from dimers up to decamers, for example. The use of di-galacturonic acid is exemplified in Scheme 5.

The pectine used as a starting material is hydrolysed by enzymatic or acidic hydrolysis to form polygalacturonic acid (α-1,4), which is then, again by enzymatic or acidic hydrolysis, hydrolysed into for example tri-galacturonic acid, i.e. compound 9 in Scheme 4, and di-galacturonic acid, i.e. compound 13, in Scheme 5.

The resulting mixture of oligogalacturonic acids can be easily separated on a large scale by ion-exchange chromatography (Ref.10).

METHOD A. ESTERIFICATION BY ETHYLENE OXIDE

The tri-galacturonic acid obtained (compound 9 in Scheme 4) is then esterified with ethylene oxide in a manner known per se (step b, Ref.11) to give the corresponding hydroxyethyl ester (compound 10 in Scheme 4).

The hydroxyethyl ester 10 is then reduced with aqueous sodium borohydride (step c, Ref. 12) to give the galactitol glycoside (compound 11 in scheme 4) which is a new and novel compound.

This new compound 11 may be acetylated using acetic anhydride to give a per-O-acetate (step d; compound 12) which is a new compound. Said compound 12 is then treated with acetic anhydride containing conc. sulphuric acid (step e; ref. 11) resulting in cleavage of the galactitol moiety without appreciable destruction of the rest of the molecule to form the fully acetylated di-galactose (compound 5 in scheme 4). Alternatively, compound 5 may be formed in one step (d and e simultaneously) using acetic anhydride and conc. sulphuric acid.

The fully acetylated di-galactose-compound 5 was isolated using the outlined procedure. Compound 5 can be used for the preparation of the free sugar (compound 1) by hydrolysis, glycosides for biological use ($\beta$-glycosides or $\alpha$-glycosides) and other conceivable derivatives containing a 4-O-$\alpha$-D-galactopyransoyl-D-galactopyranose unit as outlined in Scheme 4. It is also, of course, conceivable to prepare the glycosides from compound 1 as indicated in Scheme 4.

Scheme 4

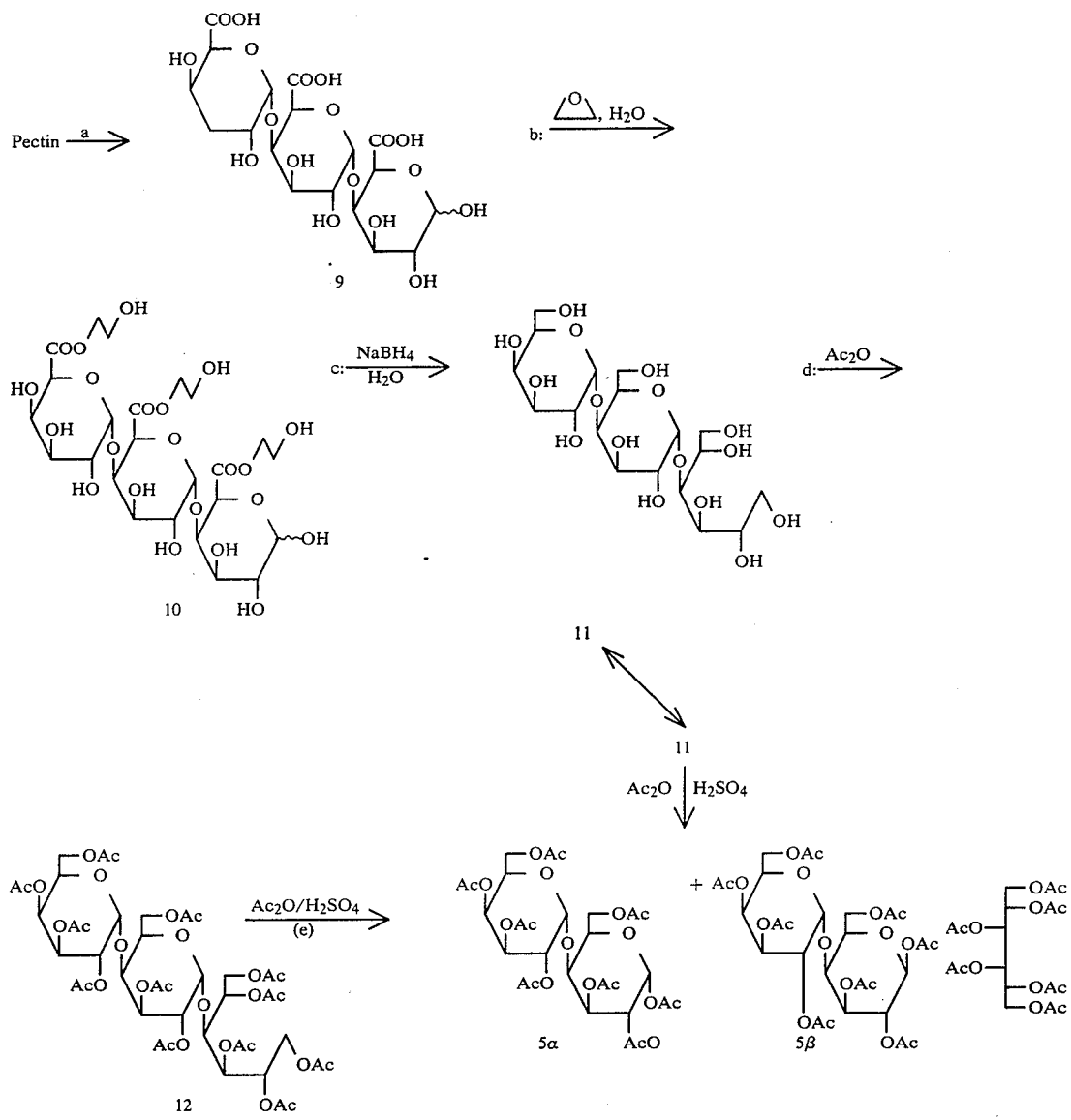

-continued
Scheme 4

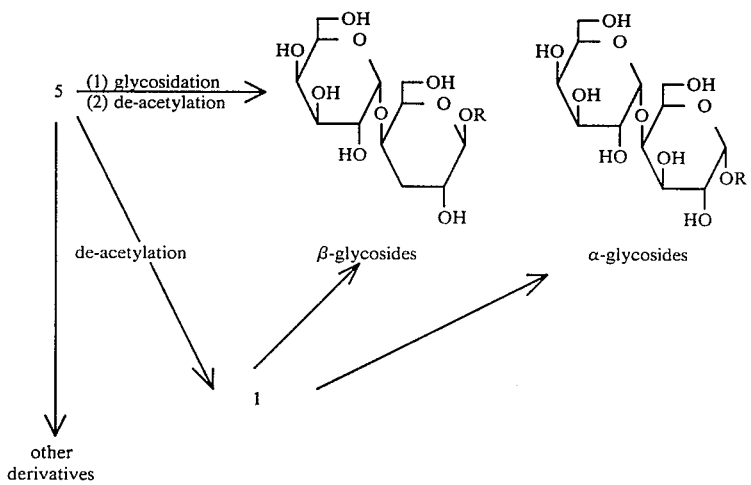

β-glycosides  α-glycosides other derivatives

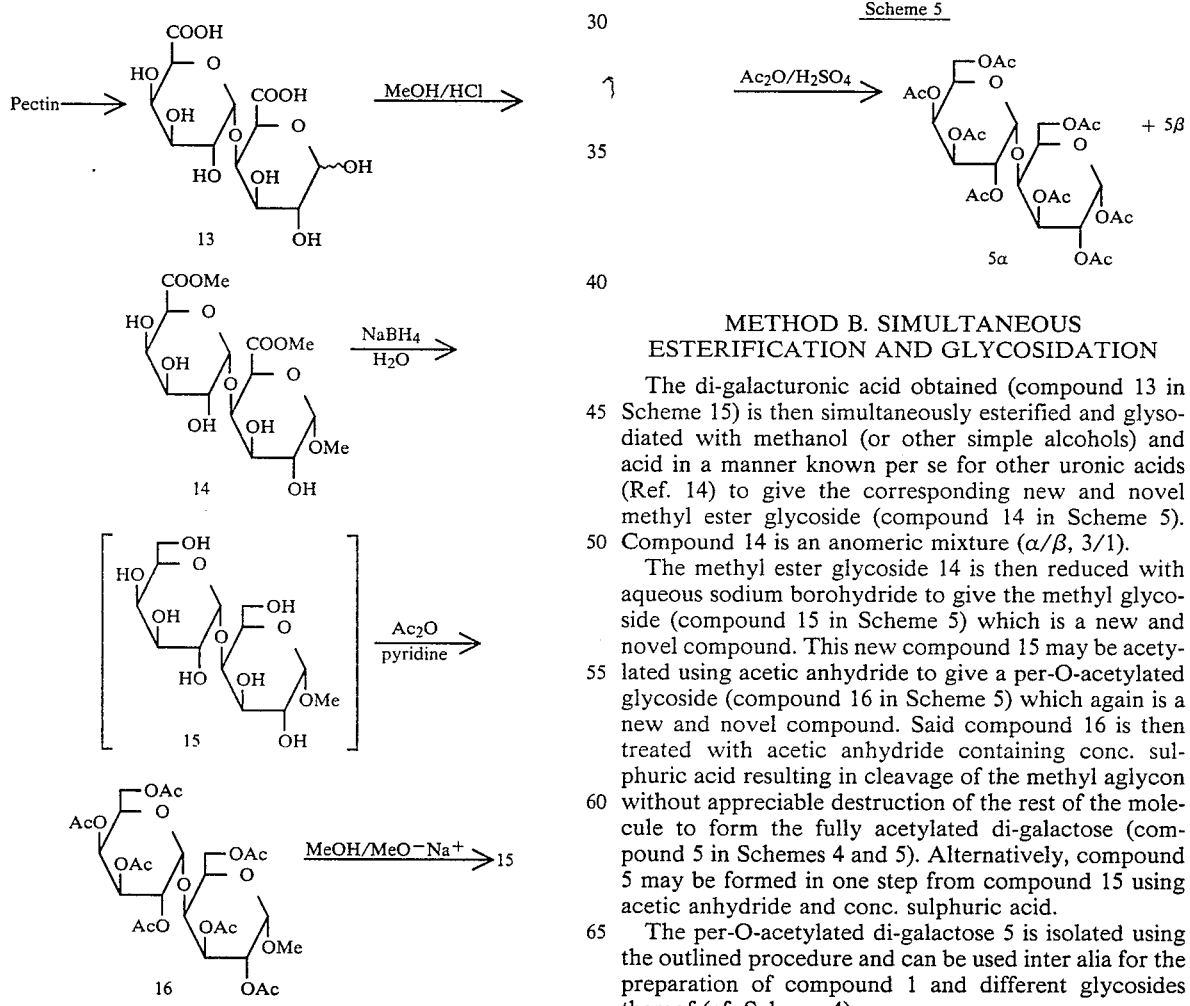

METHOD B. SIMULTANEOUS ESTERIFICATION AND GLYCOSIDATION

The di-galacturonic acid obtained (compound 13 in Scheme 15) is then simultaneously esterified and glysodiated with methanol (or other simple alcohols) and acid in a manner known per se for other uronic acids (Ref. 14) to give the corresponding new and novel methyl ester glycoside (compound 14 in Scheme 5). Compound 14 is an anomeric mixture ($\alpha/\beta$, 3/1).

The methyl ester glycoside 14 is then reduced with aqueous sodium borohydride to give the methyl glycoside (compound 15 in Scheme 5) which is a new and novel compound. This new compound 15 may be acetylated using acetic anhydride to give a per-O-acetylated glycoside (compound 16 in Scheme 5) which again is a new and novel compound. Said compound 16 is then treated with acetic anhydride containing conc. sulphuric acid resulting in cleavage of the methyl aglycon without appreciable destruction of the rest of the molecule to form the fully acetylated di-galactose (compound 5 in Schemes 4 and 5). Alternatively, compound 5 may be formed in one step from compound 15 using acetic anhydride and conc. sulphuric acid.

The per-O-acetylated di-galactose 5 is isolated using the outlined procedure and can be used inter alia for the preparation of compound 1 and different glycosides thereof (cf. Scheme 4).

EXAMPLES

The invention will be further illustrated below by the following specific examples which, however, are not to be construed as limiting.

EXAMPLE 1

Hydrolysis of polygalacturonic acid

Poly-D-galacturonic acid (50 g; Sigma) was suspended in sodium acetate buffer (1000 ml; 20 mM; pH 4.5) and the pH was adjusted with sodium hydroxide (5M). The suspension was stirred at 40° C. and pectinase (1.0 g; PV 8, Miles) was added. The hydrolysis was continued for 24 h at 40° C. and then terminated by heating at 100° C. for 5 min. Samples were withdrawn at intervals and analyzed by thin-layer chromatography. Silica gel 60; Merck. Eluant: butanol/formic acid/water 4/6/1. Visualization: the plates were dried, sprayed with sulfuric acid in ethanol (5%) and heated (105°). The major part of the hydrolysate consisted of di-, tri-, tetra-, and pentamers.

EXAMPLE II

Purification of the hydrolysis products (cf. Ref.10)

Part of the hydrolysate, containing 1,4-$\alpha$ coupled oligomers of D-galacturonic acid was passed through a column of "Zerolite" 225 (H+) cation exchange resin (600 ml of resin per 1000 ml of hydrolysate) and the eluate was lyophilized. The resulting mixture of oligomers (6 g) was dissolved in distilled water (20 ml) and the solution was applied to a column of anion exchange resin (Dowex 1×2, 50–100 mesh; formate form, equilibrated with distilled water). The column was eluted with formic acid solution (washing: 350 ml; 0.2M) followed by a concave gradient (0.2M, 2000 ml to 0.65M, 1200 ml) to give fractions containing di- and tri-galacturonic acid. Tetra-galacturonic acid was eluted with 1M formic acid solution. Freeze-drying gave the compounds in fairly pure form (>90%). The recoveries of the D-galacturonic acid oligomers are given in Table 1.

TABLE 1

Yields of D-galacturonic acid oligomers after ion-exchange chromatography of crude hydrolysate from 6 g of poly-D-galacturonic acid.

| n in (1.4-$\alpha$-D-Gal)n | (Oligomer) | Yield g (%) | Volume of eluant (ml) |
|---|---|---|---|
| 1 | (mono) | 0.2 (3) | 200 |
| 2 | (di) | 1.0 (17) | 500–1250 |
| 3 | (tri) | 2.0 (34) | 1650–3750 |
| 4 | (tetra) | 1.4 (23) | 3950–4850 |

EXAMPLE III

Preparation of 1,2,3,6-Tetra-O-(2,3,4,6-tetra-O-acetyl-$\alpha$-D-galactopyransoyl)-$\alpha$-D-galactopyranose (compound 5$\alpha$ in Scheme 4 and 5)

Method A:

Tri-D-galacturonic acid (9; 1.65 g) was dissolved in water (16.5 ml) and an excess of liquid ethylene oxide (approx 2 g) was added. The reaction mixture was stirred at room temperature for 6 days during which time ethylene oxide additions of 2–6 g were repeated five times (after 1, 2, 3, 4 and 5 days). The reaction was monitored by the rize in pH and by thin-layer chromatography (SiO$_2$: EtOAc/HOAc/H$_2$O 2/1/1).

After 6 days, when an excess of ethylene oxide was present, (pH 7) the remaining ethylene oxide was removed (water aspirator) and the reaction mixture was added dropwise during five minutes to a solution of sodium borohydride (2 g) in water (2 ml), keeping the temperature at 20°–25° C. After being stirred for 12 hours at room temperature, the reaction mixture was weakly acidified (pH 5.5) with acetic acid. The reaction mixture was filtered and the filtrate was evaporated (40° C.) several times by addition of methanol. The residue (pale yellow oil) was evaporated several times by addition of toluene and dried (oil pump pressure) to give 23 g. Ethylene glycol, sodium acetate and minor amounts of high molecular weight impurities were removed by dissolving the residue (23 g) in 45 ml of water and filtering through a column (6×55 cm) of Sephadex G-15. The separation was monitored by TLC (SiO$_2$: EtOAc/HOAc/H$_2$O 2/1/1). Fractions containing 11 ($R_f$ 0.2) were pooled and evaporated to give 1.5 g of an amorphous residue.

Acetic anhydride (50 ml), containing 1% conc. sulfuric acid, was added to the dry residue and the reaction mixture was stirred at 55° C. for eight days. The reaction was monitored by TLC. The reaction mixture was cooled, diluted with ether and extracted with water, sat. sodium-hydrogen carbonate solution and water. The ether solution was dried (Na$_2$SO$_4$) and evaporated a few times by addition of ethanol. The residue (a light-brown, "semi-crystalline" oil) was chromatographed on a column (4×60 cm) of silica gel with ethyl acetate/isooctane (3/1) as eluant. Fractions of reasonable homogeneity containing the desired product were pooled and evaporated to give 5$\alpha$ (containing a small amount of 5$\beta$). Yield: 700 mg (35%). Recrystallization from ethanol gave the pure compound (5$\alpha$; 425 mg, 21% from tri-galacturonic acid).

Method B:

Di-D-galacturonic acid (13; 20.0 g) was added to a solution of calcium chloride (20 g) in methanol (1.0 l). Duolite (H+) (15 g) was added and the mixture was refluxed for 18 h, filtered and evaporated to give crude compound 14 (Scheme 5). The residue was dissolved in water (200 ml) and a solution of sodium borohydride (6.0 g) in water (30 ml) was added during 3 minutes with occasional stirring. The reaction mixture was kept at ambient temperature for 20 h and then acidified (Dowex 50 W-X(2)), filtered, co-evaporated with methanol several times and finally dried (0.1 torr). The residue (crude compound 15; Scheme 5) was suspended in a mixture of acetic anhydride and pyridine (1:1, 600 ml), stirred at ambient temperature for 24 h and then co-evaporated with toluene several times to a thick, semi-solid, residue with no smell of pyridine. The residue was partitioned between ether (0.5 l) and water (0.2 l). The water phase was extracted with ether (2×100 ml) and the combined ether phase washed with water (50 ml), dried (Na$_2$SO$_4$) and evaporated. Co-evaporation with toluene and drying (0.1 torr) gave a pale yellow residue (31.5 g; mainly compound 16, Scheme 5). Acetic anhydride (320 ml) containing 1% conc. sulfuric acid was added to the dry residue and the reaction mixture was stirred at ambient temperature. The reaction was monitored by TLC (SiO$_2$ ether/toluene, 3/1). After being stirred for 50 min. the reaction mixture was poured into ether (1 l) and the ether solution was subsequently washed with ice-water (150 ml), sat. sodium hydrogen carbonate solution (150 ml) and ice-water (150 ml), dried (Na$_2$SO$_4$), co-evaporated with toluene and dried (0.1 torr) to give an amorphous residue (32 g). Crystallization from ethanol gave the title compound (12.3 g, 33% from di-galacturonic acid). Chromatography (SiO$_2$, EtOAc-/isooctane, 1/1) of the mother liquor, followed by crystallization from ethanol, raised the yield to 55%.

TABLE 2

Physical data for α-D-Galp-1-4-α-D-Galp(Ac)$_8$ (Compound 5α).

| source | M.p. (°C.) | $[\alpha]_D{}^t$ |
| --- | --- | --- |
| This invention | 151–154 | +135$^{21}$ (c 0.5, CHCl$_3$) |
| Total synthesis | 157–159 | +137$^{22}$ (c 1.6, CHCl$_3$) |
| Ref. 7 | 153–154 | +138$^{24}$ (c 2, CHCl$_3$) |
| Ref. 9 | 150–151 | +141$^{20}$ (c 1.0, CHCl$_3$). |

Spectroscopic data for compound 5α: $^1$HNMR (CDCl$_3$, TMS): δ 6.40 (d, 1H, J=3.5 Hz, H-1) 5.59 (d/d, 1H, J$_1$=3.0 Hz, J$_2$1 Hz, H-4'), 5.44 (d/d, 1H, J$_2$=11.0 Hz, J$_2$ 3.5 Hz, H-2), 5.40 (d/d, 1H, J$_1$=11.0 Hz, J$_2$ 3.0 Hz, H-3'), 5.25 (d/d, 1H, J$_1$=11.0 Hz, J$_2$=3.5 Hz, H-2'), 5.23 (d/d, 1H, J$_1$=11.0 Hz, J$_2$=2.5 Hz, H-3), 5.03 (d, 1H, J=3.5 Hz, H-1'), 4.54 (d/t, 1H, J$_1$=J$_2$=7.0 Hz, J$_3$=1 Hz, H-5'), 4.36 (d/d, 1H, J$_1$=10 Hz, J$_2$=6 Hz, H-6), 4.23 (t, 1H, J=6 Hz, H-5), 4.21 (d, 2H, J=7 Hz, H-6'), 4.08 (d/d, 1H, J$_1$=10 Hz, J$_2$=6 Hz, H-6), 2.15, 2.14, 2.11, 2.10, 2.06, 2.03, 2.02, 1.98. (s, 3H each).

$^{13}$CNMR (CDCl$_3$): δ170.58, 170.50, 170.32, 170.25, 170.11, 169.84, 169.49, 168.87, 99.15 (d, J=173 Hz, C-1'), 89.81 (d, J=178 Hz, C-1), 77.02, 70.37, 69.26, 68.22, 67.79, 67.29, 67.12, 66.21, 61.74, 60.62, 20.95, 20.90, 20.72(2c), 20.62(3c), 20.51.

EXAMPLE IV

Per-O-acetylated galactiol glycoside of di-galactose 5 (α-D-Galp-1-4-α-D-Galp-1-3-galactitol (Ac)12; compound 12, Scheme 4)

Compound 11 from Example III was treated with acetic anhydride containing 1% conc.sulfuric acid for 3 hours.

Work-up as above followed by chromatography (SiO$_2$, ethyl acetate/iso-octane 3/1) gave the dodeca-acetate (12) as a colorless amorphous solid.

$[\alpha]_D{}^{22}$+93° (c 1.2, CHCl$_3$). $^1$HNMR(CDCl$_3$TMS): δ 5.58 (d/d, 1H, J$_1$=3.0 Hz, J$_2$=1 Hz, H-4''), 5.54–5.10 (8H), 5.01 (d, 1H, J=3.3 Hz, H-1''), 4.54 (t, 1H, J=7 Hz, H-5''), 4.48–4.00 (11H), 2.14, 2.12, 2.11, 2.105, 2.09, 2.09, 2.085, 2.08, 2.07, 2.06, 2.03, 1.99 (s, 3H each).

$^{13}$CNMR: δ170.54, 170.43 (3c), 170.30 (2c), 170.18, 170.08, 169.97, 169,93, 169.85, 169.73, 99.23 (d, J=172 Hz), 97.79 (d, J=174 Hz), 77.56, 75.92, 70.59, 70.44, 69.06, 69.01, 68.94, 68.26, 67.78, 67.43, 67.37, 67.01, 67.27, 62.10, 61.79, 60.51, 20.99, 20.83, 20.72 (2c), 20.709 (2c), 20.706 (2c), 20.67 (3c), 20.56.

EXAMPLE V

Methyl 2,3,6-tetra-O-acetyl-4-O-(2,3,4,6-tetra-O-acetyl-α-D-galactopyranosyl)-α-D-galatopyranoside (compound 16, Scheme 5)

Part of the crude compound 16 (Example III, Method B, pale yellow residue) was crystallized from methanol to give the title compound 16 as needles. Mp. 176°–178.5°; $[\alpha]_D{}^{22}$+159.7° (c 0.9, CHCl$_3$); $^1$HNMR (CDCl$_3$, TMS): δ5.57 (broad d, 1H, J=3 Hz, H-4'), 5.40 (d/d, 1H, J$_1$=11 Hz, J$_2$=3 Hz, H-3'), 5.30–5.19 (3H, H-3, H-2, H-2'), 5.00 (broad S, 2H, H-1, H-1'), 4.54 (broad t, 1H, J=7 Hz, H-5'), 4.36 (d/d, 1H, J$_1$=13 Hz, J$_2$=9 Hz, H-6), 4.24–4.04(5H), 3.42 (S, 3H, CH$_3$O—), 2.15 (S, 6H), 2.11, 2.10, 2.09, 2.05, 2.01 (S, 3H each).

$^{13}$C-NMR(CDCl$_3$, TMS): δ170.54, 170.50, 170.42, 170.30, 170.17, 169.99, 169,40, 99.03 (d, J=172 Hz, C-1'), 97.19 (d, J=175 Hz, C-1), 77.71, 69.44, 68.28, 67.80(3C), 67.40, 66.97, 62.37, 60.64, 55.39 (CH$_3$O) 20.96, 20.80, 20.78, 20.77, 20.73, 20,66 (2C).

EXAMPLE VI

Methyl 4-O-(α-D-galactopyransoyl)-α-D-galactopyranoside (compound 15, Scheme 5)

The title compound 15 (Scheme 5 and Example III, Method B) was prepared in pure form by deacetylation of compound 16 (see Example V) according to the following procedure:

Compound 16 (2.5 g) was dissolved in warm tetrahydrofuran (10 ml). Methanol (20 ml) was added and the mixture was cooled to ambient temperature. Methanolic sodiummethylate (0.1M, 3 ml) was added and the reaction mixture was stirred for 24 h after which time the title compound had precipitated as needles. The reaction mixture was filtered and the precipitate was washed with methanol and dried (0.1 torr) to give 1.08 g (79%) of the title compound 15. M.p. 210°–211° C.; $[\alpha]_D{}^{22}$+228.3° (c 0.5, H$_2$O). $^1$H-NMR (DMSO-D$_6$, D$_2$O added, 50° C., TMS) inter alia: δ4.82 (1H, d, J=3.5 Hz, H-1') 4.59 (1H, d, J=2.5 Hz, H-1), 3.27 (3H, s, CH$_3$O)

$^{13}$C-NMR (D$_2$O, TSP): δ103.33 (d, J=170 Hz, C-1), 102.33 (d, J=170 Hz, C-1'), 81,73, 73.94, 73.85, 72.07, 72.00, 71.85, 71.47, 71.26, 63.47 (t, 2c, J=144 Hz, C-6, C-6'), 58.05 (q, J=144 Hz, CH$_3$O).

EXAMPLE VII

Methyl ester glycoside of di-D-galacturonic acid (compound 14, Scheme 5)

The title compound 14 (Scheme 5 and Example III, Method B) was prepared by chromatographic purification of the crude material formed in the first reaction step as described in Example III, Method B. The ratio between α- and β-isomers was approximately 3:1 (determined by NMR).

$^1$H-NMR (DMSO-D$_6$, D$_2$O added, 50° C., TMS) inter alia: δ4.96 (d, J=1.5 Hz, H-5), 4.93* (d, J=1.5 Hz, H-5), 4.72 (d, J=3 Hz, H-1'), 4.69 (d, J=4 Hz, H-1), 4.32 (d, J=1 Hz, H-5'), 4.29* (d, J=1 Hz, H-5'), 4.18 (d/d, J$_1$=3.0 Hz, J$_2$=1 Hz, H-4'), 4.10 (d, J=7.5 Hz, H-1) 3.92 (d/d, J$_1$=3.0 Hz, J$_2$=1.5 Hz, H-4), 3.69 (S, COOCH$_3$), 3.63 (S, COOCH$_3$), 3.42* (S, CH$_3$O), 3.29 (S, CH$_3$O).

$^{13}$C-NMR (D$_2$O, TSP): δ174.28, 173.36, 173*, 106.51*, 106.38, 103.29*, 102.52, 81.83, 81.04*, 74.17, 72.97*, 72.84, 72.75, 71.46, 71.40*, 71.39*, 70.81, 70.57, 70.75, 60.38*, 58.59, 55.85*, 55.78, 55.65.

*Signals from β-isomer

EXAMPLE VIII

4-O-α-D-galactopyranosyl-D-galactose (compound 1, Scheme 4)

Compound 5α (5 g) from Scheme 4 or 5 above was dissolved by warming in 100 ml of methanol. After cooling to room temperature 12 ml of a 0.1M solution of sodium methoxide in methanol was added (cf. ref. 14). After being kept for 4 days at room temp., the mixture was diluted with water and the methanol was evaporated. The aqueous solution was neutralized with acidic ion exchange resin [Dowex 50W-X2 (H)], treated with charcoal, filtered and evaporated. Crystallization from methanol-water gave the title compound 1 (2 g, 78%), indistinguishable from compound 1 prepared by total synthesis.

M.p. 211°–213° C.; $[\alpha]_D^{26}+171°$ (C 1, H$_2$O), Litt.[15]: m.p. 210°–211° C.; $[\alpha]_D^{26}+177°$; Litt.[7]: $[\alpha]_D^{26}+167°$ (c 1, H$_2$O).

Above there has been described reduction of compounds of formulae (III) and (V) to form compounds of formulae (IV) or (II) and (VI), respectively. In such reductions deuterium or tritium atoms can easily be introduced on the substituent carbon atoms attached in 5-position by using NaBD$_4$ or NaBT$_4$, respectively, as reducing agents. Introduction of such heavier isotopes on the carbon atoms attached in 5-position results in analytical advantages in regard to the corresponding product compounds. Thus, the introduction of deuterium atoms to replace hydrogen atoms has for a result that interference brought about by the presence of lactose in mass spectrometry measurements will be eliminated. On the other hand the introduction of tritium atoms on the said carbon atoms makes the resulting compounds detectable by radioactive measurements. Both these facts facilitate greatly the tracing of the compounds when used in test systems or in therapy or diagnostic use. The resulting compounds are, of course new and novel, and form as such another aspect of the present invention.

EXAMPLE IX

6,6-Di-deuterio-4-O-(6,6-di-deuterio-α-D-Galactopyranosyl)-D-galactose

The title compound was prepared from di-D-galacturonic acid (13) by the method described in Example III, Method B, with the only difference that sodium borohydride was replaced by sodium borodeuteride. Acetylation under acidic conditions gave the tetra-deuterated per-O-acetate analog of compound 5.

$^1$NHMR (CDCl$_3$, TMS): δ6.38 (d, 1H, J=3.5 Hz, H-1), 5.57 (d/d, 1H, J$_1$=3 Hz, J$_2$=1 Hz, H-4'), 5.41 (d/d, 1H, J$_1$=11 Hz, J$_2$=3.5 Hz, H-2), 5.39 (d/d, 1H, J$_1$=11 Hz, J$_2$=3 Hz, H-3'), 5.22 (d/d, 1H, J$_1$=11 Hz, J$_2$=3.5 Hz, H-2'), 5.24 (d/d, 1H, J$_1$=11 Hz, J$_2$=3 Hz, H-3), 5.02 (d, 1H, J=3.5 Hz, H-1'), 4.52 (broad s, 1H, H-5'), 4.22 (s, 1H, H-5), 4.21 (d, 1H, J=3 Hz, H-4), 2.16, 2.14, 2.11, 2.07, 2.04, 2.03, 2.00 (s, 3H each, CH$_3$CO).

$^{13}$CNMR (CDCl$_3$, TMS): δ170.57, 170.49, 170.33, 170.28, 170.08, 169.83, 169.44, 168.86, 99.09 (d, J=171 Hz, C-1'), 89.79 (d, J=178 H$_2$, C-1), 76.93, 70.17, 69.23, 68.19, 67.70, 67.75, 66.95, 66.14, 20.93, 20.89, 20.71 (2c), 20.61 (3c), 20.49.

Deacetylation, work-up and crystallization, as described in Example VIII, gave the title compound.

REFERENCES

1. Advances in chemotherapy, III. Symposium on bacterial attachment, Stockholm, Sweden, Jan. 23, 1981.
2. H. Leffler and C. Svanborg-Edén, *FEMS Microbiol. Lett.* 8, 127 (1980).
3. G. Källenius, R. Möllby, S. B. Svenson, J. Winberg, A. Lundblad, S. Svensson and B. Cedergren, *FEMS Microbiol. Lett.* 7, 297 (1980).
4. E. Mårtenson, *Acta Chem. Scand.*, 17, 2356 (1963).
5. J. K. N. Jones and W. W. Reid, *J.Chem.Soc.* 1955, 1890.
6. G. O. Aspinall and R. S. Fanshawe, *J.Chem.Soc.* 1961, 4215.
7. M. E. Chacon-Fuertes and M. Martin-Lomas: *Carbohyd. Res.* 43, 51 (1975).
8. P. A. Gent, R. Gigg and A. A. E. Penglis, *J.Chem.- Soc. Perkin Trans.* 1, 1395 (1976).
9. D. D. Cox, E. K. Metzner and E. J. Reist, *Carbohyd. Res.*, 62, 245 (1978). Cf. G. M. Bebault and G. G. S. Dutton, *Carbohyd. Res.* 37, 309 (1974). M. Dejter-Juszynski and H. M. Flowers, *Carbohyd. Res.*, 41, 308 (1975).
10. I. Ashby, J. Brooks and W. W. Reid, *Chem. and Ind.*, 26, 360 (1955).
11. W. W. Reid; *Meth.Carbohyd.Chem.* I, 309 (1962).
12. C. f. B. A. Lewis, F. Smith and A. M. Stephens, *Meth. Carbohyd. Chem.* II, 68 (1963).
13. M. L. Wolfrom, A, Thompson and E. Pacsu, *Meth. Carbohyd. Chem.* II, 215 (1963).
14. J. K. N. Jones and M. Stacey, *J.Chem.Soc.*, 1947, 1340.
15. R. L. Whistler and H. E. Conrad, *J.Am.Chem.Soc.*, 76, 1673 (1954).

We claim:

1. A compound having the formula (I):

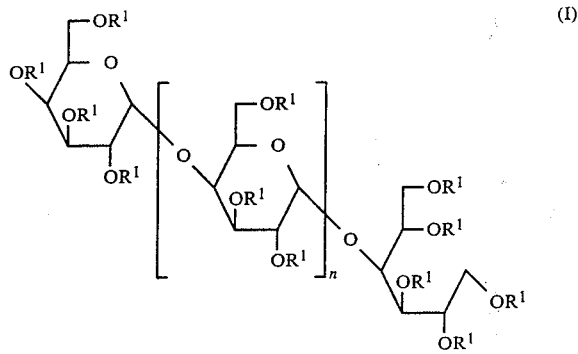

wherein R$^1$ is hydrogen or acetyl; and n is an integer of up to 10 including zero.

2. Compound according to claim 1, wherein n is 1 or 2.

3. A compound having the formula (V):

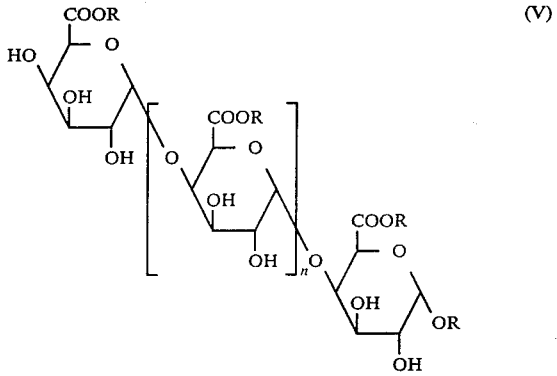

wherein n is an integer of up to 10 including zero, and R is an alkyl group having from 1 to 6 carbon atoms.

4. Compound according to claim 3, wherein n is zero or one.

5. Compound according to claims 3 or 4, wherein R is selected from the group consisting of methyl, ethyl, propyl and butyl.

6. Compounds of formula II:

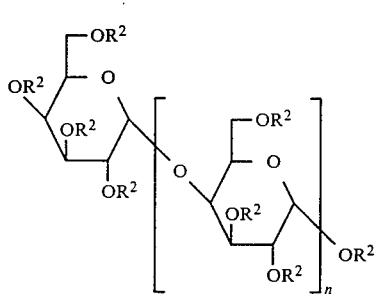
(II)

wherein R² is hydrogen or an acetyl group, and n is an integer from 1 to 10, inclusive, formula IV:

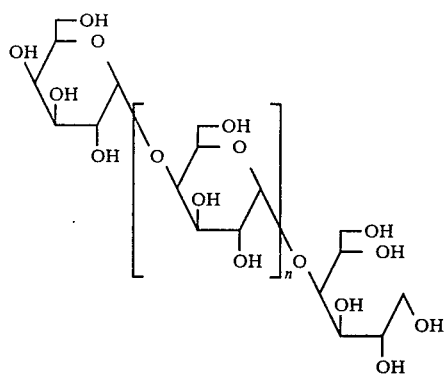
(IV)

wherein n is an integer of up to 10 including zero, or formula VI:

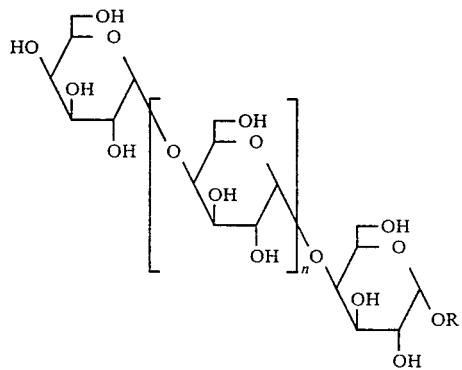
(VI)

wherein n is an integer of up to 10 including zero, and R is an alkyl group having from 1 to 6 carbon atoms, wherein the hydrogen atoms of carbon atom number 6 in each galactopyranose ring of the compounds of formula II, IV and VI have been replaced by deuterium or tritium atoms.

7. Compound according to claim 1, wherein n is 1.

8. A process for preparing a compound of formula (II):

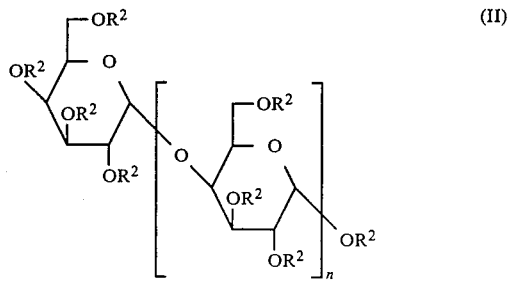
(II)

wherein R² is an acetyl group and n is 1, which comprises:

(a) hydrolyzing pectin to produce compounds of formula (IIIb) and (IIIc):

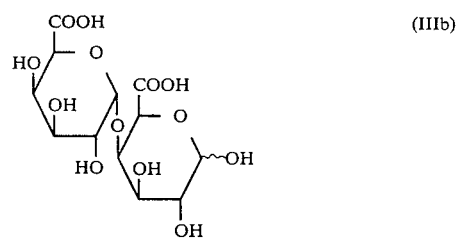
(IIIb)

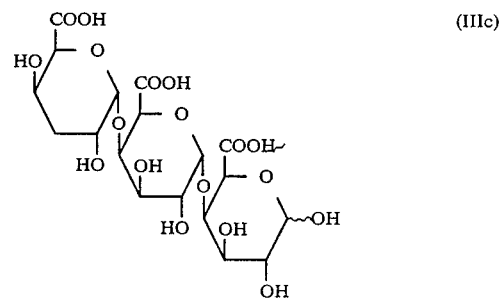
(IIIc)

(b) separating the compound of formula (IIIb) from the compound of formula (IIIc);
(c) esterifying and glycosidating the compound of formula (IIIb) with methanol;
(d) esterifying the compound of formula (IIIc) with ethylene oxide;
(e) reducing the compounds produced in steps (c) and (d) with sodium borohydride to obtain compounds of formula (IVa) and (IVb):

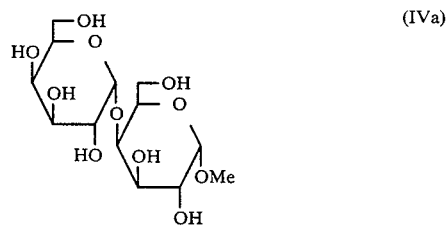
(IVa)

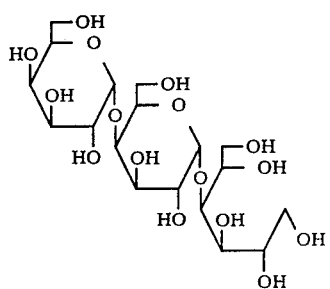
(IVb)

(f) acetylating compounds (IVa) and (IVb) with acetic anhydride and sulfuric acid to obtain the compound of formula (II) wherein $R^2$ is an acetyl group and n is 1.

9. A process for preparing a compound of formula (II):

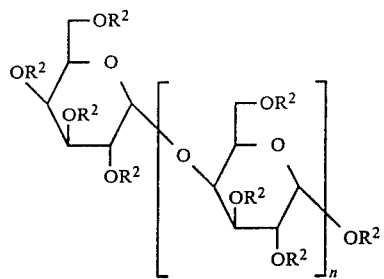
(II)

wherein $R^2$ is hydrogen and n is 1, which comprises:
(a) hydrolyzing pectin to produce compounds of formula (IIIb) and (IIIc):

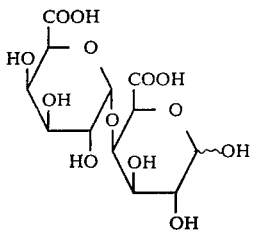
(IIIb)

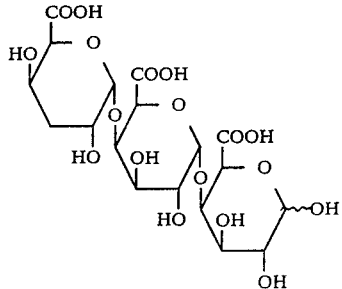
(IIIc)

(b) separating the compound of formula (IIIb) from the compound of formula (IIIc);
(c) esterifying and glycosidating the compound of formula (IIIb) with methanol;
(d) esterifying the compound of formula (IIIc) with ethylene oxide;
(e) reducing the compounds produced in steps (c) and (d) with sodium borohydride to obtain compounds of formula (IVa) and (IVb):

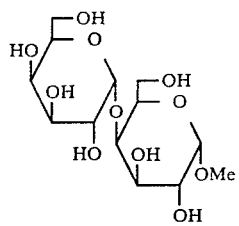
(IVa)

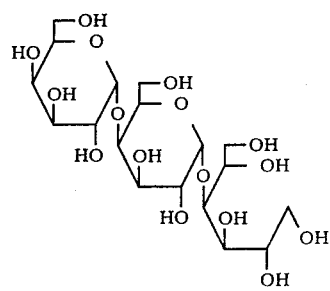
(IVb)

(f) acetylating compounds (IVa) and (IVb) with acetic anhydride and sulfuric acid; and
(g) deacetylating the product of step (f) with sodium methoxide in methanol to obtain the compound of formula (II) wherein $R^2$ is hydrogen and n is 1.

* * * * *